(12) United States Patent
Fischer et al.

(10) Patent No.: US 7,220,538 B2
(45) Date of Patent: May 22, 2007

(54) COMPOSITION FOR MAINTAINING ORGAN AND CELL VIABILITY

(75) Inventors: Joseph Fischer, Freehold, NJ (US); Jan Baker, Dixon, CA (US); Robert G. L. Shorr, Edison, NJ (US)

(73) Assignee: Lifeblood Medical, Inc., Freehold, NJ (US)

( * ) Notice: Subject to any disclaimer, the term of this patent is extended or adjusted under 35 U.S.C. 154(b) by 0 days.

(21) Appl. No.: 10/841,756

(22) Filed: May 7, 2004

(65) Prior Publication Data

US 2005/0037330 A1 Feb. 17, 2005

Related U.S. Application Data

(60) Provisional application No. 60/469,200, filed on May 9, 2003.

(51) Int. Cl.
*A01N 1/00* (2006.01)

(52) U.S. Cl. .................. 435/1.1; 435/374; 435/383; 435/384; 435/405

(58) Field of Classification Search .............. 435/1.1, 435/374, 383, 384, 405
See application file for complete search history.

(56) References Cited

U.S. PATENT DOCUMENTS

| | | | | |
|---|---|---|---|---|
| 4,533,637 A | * | 8/1985 | Yamane et al. ............. 435/371 |
| 4,657,866 A | * | 4/1987 | Kumar ....................... 435/383 |
| 4,663,289 A | | 5/1987 | Veech |
| 4,761,288 A | * | 8/1988 | Mezei ........................ 424/450 |
| 4,798,824 A | | 1/1989 | Belzer et al. |
| 4,873,230 A | | 10/1989 | Belzer et al. |
| 4,879,283 A | | 11/1989 | Belzer et al. |
| 5,066,578 A | | 11/1991 | Wikman-Coffelt |
| 5,104,787 A | * | 4/1992 | Lindstrom et al. .......... 435/1.1 |
| 5,221,668 A | * | 6/1993 | Henningfield et al. ........ 514/23 |
| 5,232,848 A | * | 8/1993 | Wolfe et al. ................ 435/406 |
| 5,405,742 A | * | 4/1995 | Taylor ........................ 435/1.2 |
| 5,468,635 A | * | 11/1995 | Komiya et al. ............. 435/404 |
| 5,474,931 A | * | 12/1995 | DiSorbo et al. ............. 435/407 |
| 5,543,316 A | * | 8/1996 | Zawadzka et al. .......... 435/366 |
| 5,599,659 A | | 2/1997 | Brasile et al. |
| 5,658,575 A | * | 8/1997 | Ribier et al. ............... 424/401 |
| 5,712,163 A | * | 1/1998 | Parenteau et al. .......... 435/405 |
| 5,756,547 A | | 5/1998 | Horwitz |
| 5,843,024 A | | 12/1998 | Brasile |
| 5,948,609 A | | 9/1999 | Carter et al. |
| 6,080,730 A | | 6/2000 | Lemasters et al. |
| 6,153,582 A | * | 11/2000 | Skelnik ........................ 514/12 |
| 6,200,590 B1 | * | 3/2001 | Eley ........................... 424/433 |
| 6,235,500 B1 | | 5/2001 | Sligar et al. |
| 6,265,180 B1 | * | 7/2001 | Zuelli et al. ................. 435/29 |
| 6,291,424 B1 | | 9/2001 | Stamler et al. |
| 6,303,375 B1 | * | 10/2001 | Kimura et al. .............. 435/395 |
| 6,372,494 B1 | * | 4/2002 | Naughton et al. .......... 435/391 |
| 6,406,909 B1 | * | 6/2002 | Shibuya et al. ............. 435/404 |
| 6,416,740 B1 | * | 7/2002 | Unger ....................... 424/9.52 |
| 2002/0012988 A1 | * | 1/2002 | Brasile ..................... 435/284.1 |
| 2002/0090369 A1 | * | 7/2002 | Murphy et al. ........... 424/94.63 |
| 2002/0119567 A1 | * | 8/2002 | Chiarello et al. ........... 435/404 |
| 2005/0123617 A1 | * | 6/2005 | Chang et al. .............. 424/490 |

FOREIGN PATENT DOCUMENTS

| | | |
|---|---|---|
| EP | 76647 A2 * | 4/1983 |
| EP | 0 377 582 A | 7/1990 |
| EP | 0 806 140 A | 11/1997 |
| JP | 04 149101 A | 5/1992 |
| WO | WO 93/09220 | 5/1993 |
| WO | WO 94/22482 | 10/1994 |
| WO | WO 98/41213 A | 9/1998 |
| WO | WO 99/28348 | 6/1999 |

OTHER PUBLICATIONS

Ranpirnase: Definition(s) from the Unified Medical Language System Diseases Database. http://diseasesdatabase.com/umlsdef.asp?glngUserChoice=33114. Accessed Feb. 8, 2006.*

Testerman, TL et al. Nutritional requirements and antibiotic resistance patterns of Helicobacter species in chemically defined media. Journal of Clinical Microbiology. 2006. 44(5): 1650-1658.*

\* cited by examiner

*Primary Examiner*—Leon B. Lankford, Jr.
*Assistant Examiner*—Susan E. Fernandez
(74) *Attorney, Agent, or Firm*—Lucas & Mercanti, LLP

(57) ABSTRACT

The present invention is directed to nanoparticle compositions for maintaining organ, tissue and cellular viability when such are separated from normal physiological supports. Compositions containing the nanoparticle compositions and methods of preserving organs such as kidneys, both in vivo and ex vivo, are also disclosed.

29 Claims, No Drawings

COMPOSITION FOR MAINTAINING ORGAN AND CELL VIABILITY

CROSS-REFERENCE TO RELATED APPLICATIONS

This application claims the benefit of priority from U.S. Provisional Application Ser. No. 60/469,200, filed May 9, 2003, the disclosure of which is incorporated herein by reference.

FIELD OF THE INVENTION

The present invention relates to compositions for the prolonged preservation of organs, tissues and cells, and particularly for the preservation of organs donated for transplant, as well as methods of making and using the same.

BACKGROUND OF THE INVENTION

Progress in the art of medical organ transplant has increased the demand for viable organs, tissues and cells from donors. Given the stringent requirements for tissue and blood type matching, and the limited sources for donations, the supply of available hearts, livers, lungs, kidneys, etc. is generally substantially less than the number of patients waiting for a life-extending transplant. Thus, there remains an ongoing need to optimize the limited supply of donated organs. One way that the art has sought to maximize the availability of donated organs is by improving the preservation of organs after donation.

Generally, current donor organ preservation protocols do not attempt to recreate an in vivo-like physiologic state for organs separated from a normal blood supply. Instead, they utilize hypothermic (below 20° C. and typically at about 4° C.) and storage in an osmotically neutral, crystalloid solution. The most common solutions for heart preservation are The University of Wisconsin Solution (UW), St. Thomas Solution, and the Stanford University Solution (SU).

This and other current methods for preserving viability of an organ that has been separated from its usual nutrient sources, e.g., the blood circulation of a living animal or person, depend on contacting and/or perfusing the organ with a supportive solution designed to provide pH buffering, osmotic balance and/or some minimal nutritional support, e.g., in the form of glucose and a limited set of other basic nutrients. This approach is typically combined with reduction in organ temperature to just above the freezing point of water. This is intended to reduce the metabolic rate of organ tissues, thus slowing the consumption of nutrients and the production of waste products. These art-known preservative solutions included, for example, isotonic saline solutions, that may contain, in various proportions, salts, sugars, osmotic agents, local anesthetic, buffers, and other such agents, as described, simply by way of example, by Berdyaev et al., U.S. Pat. No. 5,432,053; Belzer et al., and the product ViaSpan®, described by U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. Nos. 5,370,989 and 5,552,267. The ViaSpan® product data sheet describes the product as a sterile, non-pyrogenic solution for hypothermic flushing and storage of organs. The solution has a approximate calculated osmolarity of 320 mOsM, a sodium concentration of 29 mEq/L, a potassium concentration of 125 mEq/L, and a pH of 7.4.

Preservative solutions that contain pyruvate, inorganic salts supporting cell membrane potential and albumin or fetal calf serum, are described in U.S. Pat. No. 5,066,578 while U.S. Pat. Nos. 6,495,532 and 6,004,579, describe organ preservative composition that includes one or more phosphatidic acids or sugars, and lysophosphotidic acids or sugars, together with enhancers such as albumen, optionally delivered in liposomal compositions.

The storage and transport of organs supported in this way, in hypothermic storage remains limited in time. Given the ongoing shortage of donated organs, there still remains a longstanding need to extend the time for storage or transport before reimplantation. It has been hypothesized that one important cause of the short storage time for reimplantation, is damage incurred during cold storage, followed by tissue injury that occurs during warming and repurfusion with blood of the transplant recipient.

It has been proposed to remedy this problem by employing a liposome composition that includes various phospolipids to prevent apoptosis (programmed cell death) of cells or organ tissues in storage, as described, e.g., by U.S. Pat. Nos. 6,004,579 and 6,495,532. However, this proposal has not produced the sought-after improvements in viability and longevity of organs in storage. It also suffers from a number of drawbacks, including undesirable levels of uptake of phospholipids into tissues.

As can be readily appreciated, there remains a longstanding need in the art for compositions and methods for the improved preservation of viable organs, tissues and even cells for prolonged periods away from normal circulatory support, both in vivo and in vitro, that are optionally combined with suitable oxygen carriers for enhanced maintenance of tissue and cell viability.

SUMMARY OF THE INVENTION

In one aspect of the invention there is provided a two-phase composition for maintaining cellular viability. The composition includes a first phase comprising a base nutritive medium; and a second phase comprising nanoparticles having an outer lipophilic coating and an inner hydrophilic core, wherein a) the first phase comprises physiologically compatible concentrations/ amounts of water soluble or dispersible nutrients, and physiological salts;

b) the nanoparticles of the second phase comprise one or more of the following: lipids, fatty acids, sterols, free fatty acids, optional cellular growth factors; and c) the two-phase composition has an osmolality of at least about 300 mOsM/kg.

The pH of the two-phase composition is preferably from about 7.2 to about 7.4. The core portion thereof may also include a free fatty acid such as oleic acid, linoleic acid, palmitic, stearic acid, myristic acid, lauric acid, eicosapentaenoic acid, docosahexaenoic acid, and combinations thereof. Alternatively, the hydrophilic inner core can contain a solution or suspension having a moiety capable of binding and releasing oxygen such as a heme protein. In still further aspects, the hydrophilic inner core contains biologically active moiety such as a drug or other therapeutic agent. Preferably, the inventive compositions have an osmolality that is higher than that of normal body fluids, e.g., preferably at least about 300 and more preferably ranges from about 385-425 mOsM/kg.

In an alternative aspect of the invention, there is provided a three phase composition which includes the composition described above (i.e. the two phase composition) admixed with a separate nanoparticle-containing composition nanoparticles having an outer lipophilic coating and a hydrophilic inner core comprising a solution or suspension comprising a moiety capable of binding and releasing oxygen such as a heme protein or a biologically active moiety.

In further aspects of the invention there are provided processes for preparing the two phase and three phase compositions described herein, as well as methods of preserving or maintaining mammalian tissues or mammalian organ, ex vivo, in which the tissue or organ into an effective amount of the compositions described herein.

DETAILED DESCRIPTION OF THE INVENTION

Accordingly, the invention provides compositions for preserving/maintaining cells, tissues and organs in vivo, ex vivo and/or in vitro, as well as methods of making and using these compositions. Broadly, the inventive compositions include and incorporate liposomes and/or nanoparticles formulated to include supportive and/or preservative nutrients and other substances for maintaining the health and viability of cells, tissues and/or organs both in vivo and ex vivo at non-hypothermic temperature ranges, e.g., at temperatures ranging from about 20 to about 37° C. The compositions of the present invention can, of course, be employed at the hypothermic ranges commonly used in the art which can range from below 20° C. to about 4° C. Regardless of the temperature of at which the preserved organ/sample is being kept, the compositions of the present invention provide improved results when compared to those of the prior art. While such desirable results are observable when the inventive two-phase solutions are employed, further advantageous results are obtained when the optional oxygen carrier is included as part of the compositions or as part of the optionally preferable three phase compositions.

In certain optional embodiments, the inventive compositions are formulated with an oxygen carrier, e.g., an oxygen carrier that comprises a heme moiety. Preferably, this is hemoglobin or a derivative of hemoglobin incorporated into a liposome and/or nanoparticle. A few representative examples of art-known hemoglobin-based oxygen carriers are described by U.S. Pat. Nos. 5,674,528, 5,843,024, 5,895,810, 5,952,470, 5,955,581, 6,506,725, 6,150,507, 6,271,351, the disclosure of each of which is incorporated herein by reference. The amount of the hemoglobin or oxygen carrier included is described as an amount that is effective to achieve the desired therapeutic result. It will vary somewhat depending on the composition selected and the needs of the artisan but is, in most instances, present in amounts ranging from about 0.01 to about 10% of the final solution.

The invention also includes methods of treating or supporting tissues or organs in an animal or person after clinical death has occurred, but before the organ or tissue of interest is removal for donation. Any organs that require osmotic and nutritional support for optimal storage and transport benefit from the inventive compositions, both in vivo and in vitro.

The organs and tissues to be preserved by perfusion and/or contact with the inventive composition include: kidney, liver, lung, heart, heart-lung in combination, pancreas, and other organs of the digestive tract, blood vessels, endocrine organs or tissue, skin, bone, and other organs and tissues too numerous to mention.

The invention also includes methods for treating living animals or people in need of such supportive treatment. Thus, simply by way of example, the inventive compositions are useful in providing localized or systemic circulatory or perfusion support for organs or tissues acutely deprived of normal blood circulation caused by trauma, e.g., infusions or temporary circulation of the inventive compositions to support a partially severed limb, or analogous conditions, until surgical repair of damaged vasculature is achieved.

The invention further includes methods for preserving and protecting intact tissues and/or organs during surgical procedures, e.g., in situations where local blood circulation is interrupted or compromised. Such situations include, for example, perfusion of tissues or organ(s) as part of a surgical procedure requiring local or systemic circulatory interruption. The inventive compositions are also contemplated to be employed during or prior to repair of anatomical areas damaged by disease or accident, e.g., aiding in the preservation of a fully or partially severed finger or limb, prior to restoration of circulatory integrity.

It is further contemplated that the inventive compositions are useful in preserving cell, tissue and organs for both humans and animals in research settings where viable cell, organ and other culture techniques are needed for basic and applied biomedical research and/or diagnostic procedures requiring preserving tissue viability in vitro.

The term, "organ" as used herein encompasses both solid organs, e.g., kidney, heart, liver, lung, as well as functional parts of organs, e.g., segments of skin, sections of artery, transplantable lobes of a liver, kidney, lung, and the like. The term, "tissue" refers herein to viable cellular materials in an aggregate form, e.g., small portions of an organ, as well as dispersed cells, e.g., cells dispersed, isolated and/or grown from heart muscle, liver or kidney, including bone marrow cells and progeny cells, blood born stem cells and progeny, and the various other art-known blood elements, unless otherwise specified.

The term, "nanoparticle" as employed herein is defined as a two-layer emulsion particle, preferably with a lipophilic outer layer and a hydrophilic core, in a size (mean diameter) ranging from about 100 nm to about 300 nm, and more preferably in a size ranging from about 100 nm to about 200 nm.

Further, the use of singular terms for convenience in description is in no way intended to be so limiting. Thus, simply for illustration, reference to a composition comprising "a nanoparticle" includes reference to one or more of such nanoparticles, e.g., to a preparation with sufficient nanoparticles for the intended purpose, unless otherwise stated.

The Inventive Compositions

Broadly, and in most preferred aspects of the invention, the inventive compositions include two phases: an aqueous base nutritive medium and emulsion particles, e.g., liposomes or nanoparticles. The base nutritive medium includes combinations of various components, including those selected from among amino acids, salts, trace elements, vitamins, simple carbohydrates, and the like. This base nutritive medium is further supplemented with combinations of ingredients which can include buffers, antioxidants, plasma volume expanders, energy substrates, xanthine oxidase inhibitors and the like, dissolved or dispersed in an aqueous medium.

Thus, the base nutritive medium contains many nutrient and mineral factors at concentrations analogous to those found in blood, serum, plasma, and/or normal body tissues, although certain of these are not natural blood constituents. For example, the buffers are present to substitute for blood buffering systems, the dextrans and mannose provide enhanced osmolarity, above that normally provided by blood proteins, etc., glutathion is a protective agent, heparin is present to minimize blood clotting, and the Yeastolite provides supplemental vitamins.

In certain optional embodiments, the inventive compositions further include one or more art-known antimicrobial agents, such as antibiotics, antibacterials, specific antibodies and/or other art-known agents for controlling microbial contamination in organs, tissues and/or cells. Most art-known antimicrobials are referenced, in detail, by Goodman & Gilman's, THE PHARMACOLOGICAL BASIS OF THERAPEUTICS, 10th Edition, McGraw Hill, incorporated by reference herein in its entirety, with particular attention to Chapters 43-51.

In certain additional optional embodiments, the inventive compositions further include at one of the following: anticoagulant, thrombolytic, and antiplatelet drugs agents to prevent clotting or fibrin formation during organ preparation, storage and transplant, e.g., heparin and related glycosaminoglycans; dicumarol, phenprocoumon, acenocoumarol, ethyl biscoumacetate, indandione, and derivatives thereof, aspirin and dipyridamole, and the like. Non-steroidal anti-inflammatory agents are also optionally included in certain embodiments, e.g., where it is believed that inflammatory processes are etiologic in shorting the useful phase life of an organ, tissue or cells, e.g., for transplant. All of the foregoing agents are set forth in greater detain by Goodman & Gilman's, Id., as incorporated by reference. The amount of these compounds included is described as an amount that is effective to achieve the desired therapeutic result. It will vary somewhat depending on the composition selected and the needs of the artisan but is, in most instances, present in amounts ranging from about 0.01 to about 10% of the final solution.

A second phase of the inventive composition includes a lipid-aqueous emulsion that incorporates, e.g., lipids, fatty acids, sterols and, optionally, growth factors or other materials deemed essential for the viability of living cells, including vascular endothelial cells, in a particle having a lipophilic outer layer that readily crosses cell membranes, and a hydrophilic inner layer to be delivered intracellularly.

Many commercially available cell or tissue culture media products that are free of undefined proteins or animal sera, can be adapted to serve as the base nutritive medium, or starting point, for preparing the inventive composition, provided that such media are compatible with the specific requirements of the inventive composition. For example, the inventive composition preferably has the following features and elements, in addition to the above-mentioned basic cellular nutrient media:

energy substrates to replenish the intracellular ATP energy pool, and to provide for aerobic metabolism during the perfusion and preservation process;

antioxidants and/or xanthine oxidase inhibitors to mitigate reperfusion injury due to the free oxygen radicals.

A "nanoparticle" lipid emulsion or liposome component with a lipophilic outer layer and a hydrophilic inner core. This includes a lipid and/or sterol outer membrane, and essential fatty acids, and a hydrophilic inner core. The hydrophilic inner core includes essential materials such as protein-derived growth factors and optionally, additional substances, such as ATP, and the like.

In certain optional embodiments, this inner core can be include or be replaced with a suitable oxygen carrier, e.g., a heme protein or solution or suspension of heme proteins, including, for example, a naturally derived heme, a recombinant heme optionally mutated or chemically modified to have an oxygen saturation curve effective to transport and deliver oxygen and remove carbon dioxide in a harvested organ or tissue, and/or an artificial water soluble heme, to name but a few types of oxygen carriers.

Advantageously, the inventive composition contains no animal sera or undefined proteins in the most preferred embodiment.

Without meaning to be bound by any theory or hypothesis as to how the inventive composition might operate, it is believed that upon contact with cell membranes of treated cells, the hydrophobic outer layer fuses with the cell membrane, allowing the hybrophilic core of the inventive nanoparticle to be taken up by those cells into the cytoplasm, thereby delivering viability-enhancing supplemental energy compounds and essential growth factors. It is also believed that the elevated osmolality, relative to the osmolality of normal body fluids, operates to mitigate cellular swelling, and to facilitate the preservation of vascular cellular integrity.

In a preferred embodiment, the base nutritive medium includes, in physiologically suitable concentrations, salts, water soluble vitamins, amino acids and nucleotides. These include, simply by way of example, and without limitation, adenosine and its phosphates, uridine and its phosphate, other nucleotides and deoxynucleotides; B vitamins, e.g., B1, B2, B6, B12, biotin, inositol, choline, folate, and the like; vitamin coenzymes and co-factors, e.g., nicotinamide and flavin adenine dinucleotides, and their respective phosphates, coenzyme A and the like; various physiological salts and trace minerals, e.g., salts of sodium, potassium, magnesium, calcium, copper, zinc and iron; the essential amino acids, although all twenty naturally-occurring amino acids, and/or derivatives thereof, are optionally included. The base nutritive medium also includes, e.g. pH buffers, such as phosphate buffers and N-2-hydroxyethylpiperazine-N'-2-ethanesulfonic acid) ("HEPES") buffer; simple sugars, e.g., glucose; osmotic enhancers, such as any suitable dextran, mannose and the like; as well as optional miscellaneous components, such as, allopurinol, chondrotin, cocarboxylase, physiological organic acids, e.g., pyruvate, and optionally, a nutritive extract from natural sources, e.g., a yeast vitamin extract.

In one alternative embodiment, vitamin C (ascorbate) is optionally included in physiological or higher than physiological concentrations.

The second phase of the composition is a lipid-aqueous emulsion comprising liposomes or nano-scale particles with a lipophilic outer layer and a hydrophilic core. Generally, the second phase includes lipophilic components able to form and stabilize the outer, lipophilic layer, including, for example, cholesterol, phosphatidylcholine, Vitamin E, cod liver oil, etc. Additional components include lipid-based energy sources, including physiologically compatible amounts of free fatty acids such as linoleic, linolenic, oleic acid and functional equivalents.

In another preferred embodiment, the second phase also includes hydrophilic supportive endocrine factors such as hydrocortisone, thyroxine or its derivatives, and the like. Further supportive components can include, for example, cellular growth factors, e.g., epithelial and endothelial growth factors, including physiologically compatible amounts of vascular endothelial growth factor, platelet derived endothelial growth factor, epithelial growth factor, hepatocyte growth factor, platelet derived endothelial growth factor, and the like. Optionally, other factors contemplated to be included in the second phase include intercellular messengers such as prostoglandins, e.g., prostaglandin E1. Preferably, physiologically compatible surfactants and detergents are also included, e.g., one or more water-soluble surfactants, preferably an amphiphilic block copolymer with a molecular weight of several thousand Daltons, such as a polypropyleneoxide-polyethyleneoxide block copolymer surfactant (e.g., Pluronic F-68; from BASF) and/or nonionic surfactants. Suitable nonionic surfactants include, e.g., polyoxyethylene derivatives of sorbitol esters, e.g., polyoxyethylene sorbitan monooleate surfactants that are commercially available as TWEEN® (Atlas Chemical Co.). TWEEN 80® is particularly preferred. The core portion of the two-phase compositions of the invention preferably do not include a pharmaceutically significant quantity of a phosphatidic acid or sugar, or a lysophosphotidic acid or sugar.

Preparation of the Inventive Compositions

The inventive compositions are generally produced by a two-step process. The first step is to prepare specific combinations of the necessary ingredients which are used as building blocks for the final product. One key part of the first step is to prepare a premix for the first phase, which is the above-described base nutritive medium, designated as Premix-I, herein. The concluding part of this first step is to prepare a premix for the second phase, designated as Premix-II, herein, in which the desired components are premixed, dissolved and/or suspended in water. The Premix-II composition is then processed through a microfluidizer or similar such apparatus, under conditions effective to provide a finely divided emulsion, e.g., a nanoparticle-scale emulsion, with the nanoparticles having the aforementioned mean diameter of from about 100 nm to about 200 nm. The resulting emulsion composition based on Premix-II is then mixed with Premix-I, which provides various trace nutrients, and other components, to complete the production of the inventive compositions.

Preparation of the Premix Compositions

Formula I: The Tables 1-4 below summarize some of the preferred components and weight ranges for components found in one preferred embodiment containing a first phase designated herein as, Premix I, and a second phase containing the nanoparticles made from Premix II. The components listed in the Tables are the quantities preferably found in one liter of the final composition, after all processing is completed. The components are sorted into these tables for convenience of description, in order to group the components by the way in which the organ preserving composition is prepared by the examples discussed hereinbelow. Unless otherwise indicated, all quantities shown in the below Tables are in grams per liter of the final composition, i.e., the composition that includes both the aqueous phase and the emulsion phase.

TABLE 1

| Chemical Description | Gm/unit/Liter RANGE |
|---|---|
| Adenine HCl | 0.00019–0.00021 |
| B-12 | 0.00065–0.0007 |
| Biotin | 0.00000038–0.00000042 |
| Cupric Sulfate | 0.00000124–0.00000137 |
| Ferric Nitrate | 0.000048–0.000053 |
| Ferric Sulfate | 0.00048–0.000053 |
| Putrescine HCl | 0.000077–0.000085 |
| Pyridoxine HCl | 0.000029–0.000033 |
| Riboflavin | 0.00021–0.000231 |
| Thymidine | 0.00035–0.00039 |
| Zinc Sulfate | 0.00041–0.000454 |

TABLE 2A

| Chemical Description | Gm/unit/Liter RANGE |
|---|---|
| Adenosine | 0.950–1.050 |
| Adenosine 5' Monophosphate | 0.0019–0.0021 |
| Adenosine Triphosphate | 0.0019–0.0021 |
| Allopurinol | 0.133–0.147 |
| B' Nicotinamide Adenine Dinucleotide Phosphate | 0.038–0.042 |
| B'Nicotinamide Adenine Dinucleotide | 0.0019–0.0021 |
| Calcium Chloride | 0.152–0.168 |
| Choline Chloride | 0.0085–0.0094 |
| Chondrotin Sulfate | 0.0038–0.0042 |
| Cocarboxylase | 0.038–0.042 |
| Coenzyme A | 0.0095–0.00105 |
| Cyclodextrin | 0.475–0.525 |
| Deoxyadenosine | 0.038–0.042 |
| Deoxycytidine | 0.038–0.042 |
| Deoxyguanosine | 0.038–0.042 |
| Dextran 70 | 33.25–36.75 |
| Flavin Adenine Dinucleotide | 0.038–0.042 |
| Folic Acid | 0.0026–0.0028 |
| Glucose | 3.800–4.200 |
| Glutathione | 0.950–1.050 |
| Glycine | 0.0179–0.0197 |

TABLE 2B

| Chemical Description | Gm/unit/Liter RANGE |
|---|---|
| Heparin | 0.171–0.189 |
| HEPES | 3.396–3.753 |
| Hypoxanthine | 0.002–0.0022 |
| Inositol | 0.0124–0.0137 |
| Insulin | 0.0095–0.0105 |
| L-Alanine | 0.00428–0.00473 |
| L-Arginine | 0.141–0.155 |
| L-Asparagine | 0.0076–0.0084 |
| L-Aspartic Acid | 0.064–0.070 |
| L-Cysteine | 0.0297–0.0329 |
| L-Cystine | 0.0167–0.0185 |
| L-Glutamic Acid | 0.007–0.0078 |
| L-Glutamine | 4.750–5.250 |
| L-Histidine | 0.030–0.033 |
| L-Isoleucine | 0.052–0.0572 |
| L-Leucine | 0.057–0.063 |
| L-Lysine | 0.0095–0.0105 |
| L-Methionine | 0.019–0.021 |
| L-Phenylalanine | 0.0337–0.0373 |
| L-Proline | 0.0164–0.0182 |
| L-Serine | 0.025–0.0276 |
| L-Threonine | 0.051–0.056 |

TABLE 2C

| Chemical Description | Gm/unit/Liter RANGE |
|---|---|
| L-Tryptophan | 0.009–0.0095 |
| L-Tyrosine | 0.053–0.059 |
| L-Valine | 0.050–0.055 |
| Magnesium Chloride | 0.058–0.0643 |
| Magnesium Sulfate | 0.0475–0.0525 |
| Mannose | 3.135–3.465 |
| Niacinamide | 0.0019–0.0021 |
| Pantothenic Acid | 0.0021–0.0024 |
| Potassium Chloride | 0.296–0.328 |
| Pyridoxal HCl | 0.0019–0.0021 |
| Pyruvic Acid | 0.209–0.231 |
| Sodium Bicarbonate | 1.140–1.260 |
| Sodium Chloride | 6.650–7.350 |
| Sodium Phosphate Dibasic | 0.0676–0.0748 |
| Sodium Phosphate Monobasic | 0.0516–0.0570 |

TABLE 2C-continued

| Chemical Description | Gm/unit/Liter RANGE |
|---|---|
| Thiamine | 0.0021–0.0023 |
| Transferrin | 0.00475–0.00525 |
| Uridine | 0.038–0.042 |
| Uridine Triphosphate | 0.038–0.042 |
| Yeastolate Ultra-Filtered (Sigma Chemical Company, Cat. No. Y2000) | 38–42 ML |

TABLE 3

| Chemical Description | Gm/unit/Liter RANGE |
|---|---|
| L-Cystine | 0.0167–0.0185 |
| L-Tyrosine | 0.053–0.059 |

TABLE 4

| Chemical Description | Gm/unit/Liter RANGE |
|---|---|
| Cholesterol | 0.00475–0.00525 |
| Cod Liver Oil | 0.00095–0.00105 |
| Epithelial Growth Factor | 0.00000285–0.00000315 |
| Hepatocyte Growth Factor | 0.0000048–0.0000053 |
| Hydrocortisone | 0.00095–0.00105 |
| Linoleic Acid | 0.00095–0.00105 |
| Linolenic Acid | 0.00095–0.00105 |
| Oleic Acid | 0.00095–0.00105 |
| Phosphatidylcholine | 0.6% |
| Platelet Derived Endothelial Growth Factor | 0.00000095–0.00000105 |
| Pluronic F-68 | 0.950–1.050 |
| Prostaglandin E1 | 0.000042–0.0000263 |
| Triiodo-L-Thyroxine | 0.00000475–0.0000053 |
| TWEEN 80 ® | 0.002375–0.002625 |
| Vascular Endothelial Growth Factor | 0.0000046–0.00000525 |
| Vitamin E | 0.0019–0.0021 |

Component quantities set forth by Tables 1-4 are based upon a total batch volume of 1 liter. As exemplified herein, the 1 liter batch volume is the end volume after both Premix-I and Premix-II are combined, after Premix-II has been processed into a microscale or nanoscale emulsion. The artisan will appreciate that the processes described are readily scaled up or down for smaller or larger batch sizes, depending on need.

All chemicals used in the preparation of the inventive composition are of substantial purity and available from numerous commercial suppliers of biochemicals. Preferably, these are of USP grade or equivalent. The artisan will appreciate that the employed chemicals are optionally substituted by substantially equivalent chemicals demonstrating the same purity and activity.

TABLE 5

| | |
|---|---|
| Analytical balance; | Top loading macro balance; |
| Magnetic stir plate; | Various mixing vessels; |
| WFI grade water;* | Pipettes and other standard lab utensils; and Microfluidizer Processor model HC-5000 - Microfluidics Corporation. |

*Water for injection, preferably USP grade.

Additional miscellaneous reagents include: 5N NaOH, 5N HCl, that are employed for pH titration, and 95% pure ethanol ("EtOH").

Process For Making Premix-I

Premix-I is prepared by dissolving or dispersing components in an order that is effective to achieve a uniform and clear aqueous composition, while avoiding undesirable reactions or to the formation of insoluble complexes. For this reason, the components of Premix-I are preferably not mixed together until all are fully dissolved or dispersed in water. Preferably, as exemplified herein, the components listed by Tables 1, 2A-2C and Table 3, are processed into three different starting solutions, respectively, although the artisan will appreciate that this base composition is optionally prepared by variations on the exemplified scheme. The starting based on the individual Table 1, 2A, 2B, 2C and 3 component solutions are then combined to prepare Premix-I, which constitutes the non-emulsion base nutritive medium.

Process For Making Premix-II

Premix-II includes the emulsion-forming components of the inventive composition. Broadly, these include the hydrophilic layer of the resulting emulsion particle, e.g., components that it is desired to be delivered intracellularly in an organ, tissue or cell to be treated according to the invention. Premix-II also includes the components that form the hydrophobic layer of the resulting emulsion particle, e.g., a lipophilic outer layer that allows fusion with living cell membranes for delivery of the hydrophilic core contents, including supportive endocrine factors, suitable agents to aid emulsification, e.g., wetting agent(s) and/or a block copolymer detergent, as well as hydrophobic phase components, such as cholesterol and/or phosphorous derived lipids. Preferably, these are as listed by Table 4, supra and are combined as described by the Examples below.

II. Microfluidation

The technique of high pressure homogenization, at pressures at or above 5000 psi is art-known as "microfluidation." This process was used to create liposomes or nanoparticles with a uniform size distribution of a mean diameter of preferably from about 100 nm to about 300 nm and more preferably from about 100 nm to about 200 nm. In alternative aspects of the invention, the particles have a mean diameter of less than 200 nm. In addition to microfluidation, other standard emulsification methods are optionally employed, e.g., sonication, valve homogenization [Thornberg, E. and Lundh, G. (1978) J. Food Sci. 43:1553] and blade stirring, etc. Desirably, a water-soluble surfactant, preferably an amphiphilic block copolymer with a molecular weight of several thousand Daltons, such as a polypropyleneoxide-polyethyleneoxide block copolymer surfactant (e.g., Pluronic F-68 that is commercially available from BASF) and/or TWEEN 80, is added to the aqueous solution in order to stabilize the coated particles against aggregation as they form. The surfactant also serves to enhance the effect of (ultra)sonication, if that method is employed.

A preferred apparatus for microfluidation as exemplified herein is the Microfluidizer No. HC5000V (Microfluidics Corp., Newton, Mass.) using compressed air supplied by an encapsulated air compressor, e.g., No. ES-6 from Sullair Solutions (Michigan City, Ind.). The above-described apparatus employs high pressure and high shear homogenization to treat and emulsify the Premix-II composition and provide the nanoparticles within the desired size range.

In brief, the Premix-II composition, was processed by high pressure homogenization using the microfluidizer. The Premix-II was added to the microfluidizer reservoir in a continuous fashion, and forced through the specially designed cavitation or interaction chamber, where high shear stress and cavitation forces formed a highly divided emulsion. Through multiple cycles, the mean droplet or liposome size, distribution, and combination of ingredients yielded the desired end product, e.g., the preferred nanoparticles.

Further details of the operation of the microfluidizer Model No. HC5000V are provided by the manufacturer's operating manual, available from Microfluidics Corporation, as Cat. No. 85.0112, incorporated by reference herein in its entirely.

A second formulation (Formula II) according to the present invention is based on the materials found in Tables 6-10 below. Directions for preparing the same are provided below and in the Examples.

TABLE 6

| CHEMICAL DESCRIPTION | GMS (units)/LITER RANGE |
|---|---|
| Soy Hydrolysate[1] | 6.0–10.0 |
| Glutathione Reduced[1] | 0.008–0.020 |
| Vitamin A Acetate[2] | 0.0002–0.0003 |
| Vitamin C (Ascorbic Acid)[1] | 0.040–0.060 |
| Vitamin E Tocopherol[2] | 0.00002–0.00003 |
| Catalase[1] | 0.040–0.060 |
| SOD[1] | 0.040–0.060 |
| L-Cysteine HCl[1] | 0.040–0.060 |
| Taurine[1] | 0.025–0.040 |
| Methionine[1] | 0.015–0.030 |
| Zinc Sulfate[3] | 0.0008–0.0009 |
| Selenium[3] | 0.000025–0.000035 |
| Cupric Sulfate[3] | 0.0000045–0.000006 |
| Ethanolamine[2] | 0.0025–0.005 |
| Mercaptoethanol[2] | 0.003–0.006 |

Preparation instructions for Table 6:
1. Weigh out 1 and dissolve with mixing in WFI water
2. Weigh out 2 and dissolve in 95% ETOH
3. Prepare 1000×concentrates of components 3 in WFI
4. Mix group 1 and 2 together and add 1 ml per liter of final batch volume of group 3 to this solution.

TABLE 7A

| CHEMICAL DESCRIPTION | GMS (units)/LITER RANGE |
|---|---|
| Sodium Gluconate | 18.500–25.000 |
| Potassium Phosphate | 3.000–4.500 |
| Magnesium Sulfate | 1.000–1.500 |
| Calcium Chloride | 0.100–0.150 |
| Sodium Phosphate Monobasic | 0.250–0.350 |

TABLE 7B

| CHEMICAL DESCRIPTION | GMS (units)/LITER RANGE |
|---|---|
| L-Arginine HCl | 0.065–0.080 |
| L-Aspartic Acid | 0.050–0.065 |
| L-Glutamic Acid | 0.100–0.160 |
| L-Glutamine | 0.300–0.400 |
| Glycine | 0.045–0.060 |
| L-Histidine HCl—$H_2O$ | 0.155–0.170 |
| L-Isoleucine | 0.025–0.030 |
| L-Leucine | 0.045–0.055 |
| L-Lysine HCl | 0.240–0.300 |
| L-Phenylalanine | 0.045–0.055 |
| L-Proline | 0.045–0.055 |
| L-Threonine | 0.065–0.075 |
| L-Tryptophan | 0.035–0.0450 |
| L-Valine | 0.055–0.070 |
| L-Cystine | 0.018–0.024 |
| L-Tyrosine | 0.050–0.060 |

Preparation instructions for Table 7:
1. Weigh out all chemicals and dissolve with mixing in WFI.
2. Add to solution in Table 6

TABLE 7C

| CHEMICAL DESCRIPTION | GMS (units)/LITER RANGE |
|---|---|
| Glucose | 4.500–6.000 |
| Mannose | 8.000–12.000 |

Preparation instructions for Table 8:
1. Weigh out all chemicals and dissolve with mixing in WFI
2. Add to solution in Table 6

TABLE 8

| CHEMICAL DESCRIPTION | GMS (units)/LITER RANGE |
|---|---|
| Biotin[1] | 0.000015–0.00003 |
| Choline Bitartrate | 0.40–0.50 |
| Folic Acid[1] | 0.00035–0.0005 |
| Inositol | 0.0008–0.002 |
| Niacinamide | 0.0008–0.002 |
| Pantothenic Acid | 0.0008–0.002 |
| Pyridoxine | 0.0008–0.002 |
| Riboflavin[1] | 0.0008–0.002 |
| Thiamine | 0.008–0.015 |
| Vitamin B-12 | 0.000015–0.0003 |
| Adenosine | 0.85–1.50 |

Preparation instructions for Table 8:
1. Weigh out group 1 and dissolve in small amount of 5 NAOH and WFI
2. Weigh out remaining components and dissolve with mixing in WFI
3. Add group 1 to solution in step 2 and mix.
4. Add this solution to solution in Table 6

TABLE 9

| CHEMICAL DESCRIPTION | GMS (units)/LITER |
|---|---|
| ETOH 95% | 8.00–16.00 ml |
| Soy Hydrolysate | 3–8 ml |
| Phosphatidyl Choline | 0.00095–0.010 |
| Arachadonic Acid | 0.0000015–0.00002 |
| Linoleic Acid | 0.000095–0.00015 |
| Linolenic Acid | 0.000095–0.00015 |
| Myristic Acid | 0.000095–0.00015 |
| Oleic Acid | 0.000095–0.00015 |
| Palmitic Acid | 0.000095–0.00015 |
| Stearic Acid | 0.000095–0.00015 |
| Cholesterol | 0.002–0.004 |
| Vitamin E Tocopherol | 0.0006–0.0008 |
| Tween 80 | 0.020–0.030 |
| Pluronic F-68 | .010–1.000 |

Preparation instructions for Table 9:
1. The contents of Table 9 were subjected to the same microfluidization step mentioned above for Formulation I, Premix II
2. Add with mixing to solution in Table 6 with mixing

TABLE 10

| CHEMICAL DESCRIPTION | GMS (units)/LITER RANGE |
|---|---|
| Dextran 70 or other colloid combinations e.g. hydroxyethylstarch (HES), Human Serum Albumin, Plasma | 45.000–55.000 |

Preparation instructions for Table 10:
1. Weigh out chemicals and dissolve in WFI until dissolution is complete.
2. Add to solution in Table 6.
3. QS with WFI to final batch volume and mix.

Adjust pH with 5N NAOH or 5N HCl to pH 7.0-7.2

EXAMPLES

The following examples serve to provide further appreciation of the invention. These examples are not meant in any way to restrict the effective scope of the invention. In each case where solutions were prepared, the amount of each component included was the midpoint of the range expressed in the respective Table referred to.

Example 1

Preparation of Premix-I

Preparation of Solution 1: Using an appropriate balance, a 10,000× concentrate of each component (using the midpoint of the stated range) listed in Table 1, supra, was prepared. The amount of each component included was the midpoint of the range expressed in the Table. As a convenience, stock solutions for several of these components were prepared in advance, as follows, and an appropriate quantity of stock solution was mixed into Solution 1.

Cupric Sulfate Stock Solution at 100,000× concentration.

0.130 gms of cupric sulfate was weighed and mixed into 1000 ml of WFI gradewater. When necessary, 5N HCl was added dropwise, with mixing, until dissolution was complete. This was mixed until dissolved, and stored at −20° C.

Ferric Sulfate, Ferric Nitrate, and Zinc Sulfate Stock Solution at 10,000× Concentration.

The stock solution was prepared by weighing out 5.0 gms ferric sulfate, 0.5 gms ferric nitrate, and 4.3 grams zinc sulfate into 1000 ml of WFI grade water. When necessary, the pH was reduced to aid dissolution by adding 5N HCl dropwise until dissolution was complete. This solution was stored at −20° C. 0.1 ml per liter of batch (final volume of end product) was used.

Biotin Stock Solution at 100,000× Concentration.

The biotin stock solution was prepared by weighing out 0.040 gms of biotin into 5 ml of WFI grade water. 5N HCl was added dropwise, as needed, during mixing, until dissolution was complete. QS to 1000 ml, and stored at −20° C. 0.01 ml per liter in final solution was used.

Vitamin B-12 and Thymidine Stock Solution at 100×.

This stock solution was prepared by weighing out 0.670 gms vit. B-12 and 0.370 gms of thymidine into 1000 ml of WFI grade water, and mixing until dissolution was complete, and stored at −20° C. 1 ml per liter in final solution was used.

Once all stock concentrates were made they were added to solution 2 at a volume consistent with their concentration e.g. 1000×=1 ml per liter etc. The additional components were then added to 1000 ml of WFI grade water and mixed on a magnetic stir plate until dissolution was completed. The resulting solution was added to Solution 2, described below, at a ratio of 0.1 ml per liter of final batch volume (end product).

PREPARATION OF SOLUTION 2: Using the appropriate balance, each component (measured to the midpoint of the stated range) listed in Tables 2A, 2B and 2C was weighed and added to approximately 50% of the final volume of WFI grade water in final batch volume, i.e., for a 1 liter final batch, solution 2 was prepared to approximately 500 ml of WFI grade water. This was mixed until dissolution was complete.

PREPARATION OF SOLUTION 3: Using the appropriate balance, each component listed by Table 3 was weighed (using the midpoint of the stated range) and added to an appropriate sized mixing vessel containing 5% of total batch volume of WFI grade water. While mixing, 5N NaOH was added in a dropwise fashion, until the mixture became clear, indicating complete dissolution.

Premix-I was then prepared by taking Solution 1, and combining it with Solution 2, with mixing, in a ratio of 0.1 ml per liter of final batch volume (end product) to form a combined (1+2) solution. Then, the entire batch of Solution 3 was mixed with the (1+2) solution to produce Premix-I, that may be used immediately or stored.

Example 2

Preparation of Premix-II

Component quantities for Premix-II using the midpoint of the stated range as set forth in Table 4, supra. For convenience, a number of components of Premix-2 were first prepared as stock solutions, and then employed in appropriate volumes for preparation of Premix-II. The stock solutions were as follows.

Endocrine Factors Stock Solution at 10,000×.

This stock solution was prepared by weighing out 0.052 gms HGF, 0.050 gms triiodo-L-thyroxine, 0.050 gms VEGF, and 0.030gms EGF into 1000 ml of WFI grade water, with mixing until dissolution was complete. Batch size was calculated at ×0.1 ml and add to solution in step 4/treatment 4. Stored at −20° C. 0.1 ml per liter in final solution was used.

Hydrocortisone Stock Solution at 100×.

This stock solution was prepared by weighing out 0.95 gms of hydrocortisone into 10 ml of 95% EtOH and mixing until dissolution was complete. Batch size was calculated at ×1 ml and the stock solution was added to the solution in step 2, below. Stored at 2-8° C. 1 ml per liter in final solution was used.

Prostaglandin E1 Stock Solution ("PGE1")@ 100×.

Prepared by weighing out 0.034 gms PGE1 into 100 ml of WFI grade water and mixed until dissolution completed. Calculated batch size X 1 ml and added to solution in step 4, below. Stored at −20° C. 1 ml per liter in final solution was used.

PDGF Stock Solution at 100,000×.

This stock solution was prepared by weighing out 0.095 gms PDGF into 1000 ml WFI grade water and mixing until dissolution was complete. Batch size was calculated at ×0.01 ml and added to solution in step 4, below. Stored at −20° C. 0.01 ml per liter in final solution was used.

Premix-II was then prepared by the following steps with components (measured at the midpoint of the stated ranges as set forth in Table 4, supra.

(1). The Pluronic F-68 solution was prepared by weighing out 1 gram into less than 50% of total batch volume (based on a 1 liter batch of final product, this was less than 500 ml) of WFI grade water. This was mixed for approximately 1 hour under low heat (less than 100 degrees C.). Mixing was continued until dissolution was complete. The resulting aqueous composition was cooled to approximately 35-40° C. before use.

(2). 10 ml of 95% EtOH was measured into a glass mixing vessel and placed on a magnetic stir plate. Phosphatidylcholine was weighed, according to Table 4 (midpoint of range), and added to this solution, followed by mixing for 1 hour.

(3). Cholesterol, linoleic acid, linolenic acid, Vitamin E, TWEEN 80, cod liver oil, hydrocortisone, and oleic acid were weighed to the midpoint of the range, stated in Table 4. Preferably, these can be prepared first as a 10,000× concentrate or stock solution to achieve the desired working concentration. These were added to the solution of step 2 and mixed for 1 hour.

(4). The solutions of step 2 and 3 were added to the solutions of step 1 and mixed for 1 hour. The resulting composition appeared opaque and cloudy.

(5). Hepatocyte growth factor ("HGF"), triiodo-L-thyroxine, prostaglandin E1, vascular endothelial growth factor ("VEGF"), epithelial growth factor ("EGF"), platelet derived endothelial growth factor ("PDGF") were weighed to the midpoint of the expressed range as indicated. Preferably, these are prepared as a working stock solution of these chemicals.

(6). The ingredients of step 5 were added to the solution of step 4 and mixed for 1 hour to produce a Premix-II liquid composition.

Example 3

Formula-I: Cholesterol-based Nanoparticles by Microfluidation

Formula I was prepared from the Premix-I and Premix-II compositions of Examples 1 and 2, supra, as follows.

(1) The air compressor was turned on and the line pressure adjusted to 120 PSI@ 100 CFM. This automatically charged the pressure chamber of the microfluidizer with compressed air.

(2) The microfluidizer pressure was adjusted to 5000 PSI.

(3) The Premix-II prepared in Example 2 was added to the machine reservoir and the microfluidizer controls were turned to the full-on setting.

(4) The Premix-II passed through the active cavitation chamber and exited into a collection vessel.

(5) When all of the Premix-II was processed and collected, one cycle was completed.

(6). Steps (1)-(5) were repeated four times, and/or until the processed liquid composition emerged into the collection vessel with a clear appearance.

(7). The liquid composition was then aseptically filtered through a 0.2 micron membrane filter and stored at 4-8 degrees C. until use.

(8) The product of step (7), above, was then slowly mixed with the Premix-I, prepared in Example 1, supra so as to avoid foaming and disassociation of chemical constituents. The final ration of the Premixes was about 1:1.

(9). QS the final solution to the desired batch volume with WFI grade water, based on Tables 1-4, the final batch volume was 1 liter and the pH was adjusted to 7.2+/−0.2.

The final inventive composition was then aseptically filtered through a 0.2 micron membrane into a sterile container for storage. It appeared as an opaque milky white solution free of any particulate matter. The vesicle size has a great influence on the optical appearance of the nanoparticle dispersion. The smaller the particle the more transparent the solution will appears.

Example 4

Organ Preservation Comparison with Viaspan®

The efficacy of Formula-I, prepared in Example 3, for kidney preservation was confirmed and was evaluated relative to the preservative properties of the previous "gold standard" VIASPAN® (Barr Laboratories, Inc.).

Materials and Methods

A single outbred male hound between the ages 1-2 years was bilaterally nephrectomized and then immediately euthanized while under general anesthesia.

The left kidney was flushed with VIASPAN® and the right kidney was flushed with Formula-I. Each kidney was flushed until the fluid ran clear, as 100% flush solution, with no trace of blood or other waste material. Each kidney was flushed with 50 ml of solution /kg of weight. A biopsy of each respective kidney was taken immediately after it was flushed with solution. All biopsies were wedges of the outer cortex and greater curvature of the kidney.

Each kidney was then placed in a container containing the identical solution employed for the flush (either VIASPAN® or Formula-I). The individual container was placed in a chiller box opened only for biopsies.

Subsequent biopsies were taken at 1, 4, 8 and 24 hours after submersion in either VIASPAN® or the inventive study solution. Kidney biopsies preserved in 10% formalin were sent to Pathology Associates, a Division of Charles River Laboratories, Inc. for histolopathological evaluation Results Results of the microscopic evaluations of the biopsies at different time points are presented in Table 6, below:

TABLE 6

Histopathological Evaluation of Kidney Biopsies
Biopsy Samples

| | FORMULA -I (Right Kidney) | | | | | VIASPAN ® Solution (Left Kidney) | | | | |
|---|---|---|---|---|---|---|---|---|---|---|
| Microscopic Findings | R-Base | R-H1 | R-H4 | R-H8 | R-H24 | Left Base | Left H1 | Left H4 | Left H8 | Left H24 |
| Inflammation Mononuclear | 1) | N | N | N | 1> | 1) | | | | 1> |
| Tubular Degeneration | | | | | | | 1) | | | |
| Inflammation Acute | | | | | | | 1) | 1> | 1> | |
| Periglomerular Fibrosis | | | | | | | | | | 1) |
| Degeneration, Vascular | | | | | | | | | | |

Codes:
N = Normal; P = Present; 1+ Minimal; ) = Focal; > = Multifocal Hours = H; Right = R-

All of the biopsy specimens consisted of cortical derived tissue. In addition, perfusion artifacts such as dilation of Bowman's space and tubular dilation were present to a moderate degree in the 8 and 24 hour biopsy specimens from the right kidney. Perfusion artifact also was present in the 4 hour biopsy specimen from the right kidney but was less pronounced than in the previously mentioned specimens from the same kidney. The minor degenerative and inflammatory changes noted in some of the biopsy specimens are inconsequential. Minimal acute inflammation was present in the renal capsule of the left kidney from the 4 and 8 hour samples.

Summary

Preservation was similar for specimens from both kidneys from the baseline and 1 hour samples. Preservation was superior for the biopsy specimens taken from the right kidney (preserved with the inventive composition) for 4, 8, and 24 hour time points.

Example 5

Preparation of Premix I—Using Formula II

Preparation of Solution 1: The Ascorbic cid, catalase, SOD, L-cysteine, taurine and methionine were weighed out and dissolved with mixing in WFI water. Next, the vitamin E and mercaptoethanol were dissolved in 95% ETOH. 100× concentrates of components zinc sulfate, selenium and cupric sulfate were made. The first two groups of materials were mixed and 1 ml per liter of final batch volume of the concentrates were added to this solution. 25 grams/liter of dextran 70 and HSA were added to the solution. Each ingredient used was measured to the midpoint of the range listed in Table 6.

Preparation of Solution 2: Using the appropriate balance, each component (measured to the midpoint of the stated range) listed in Tables 7A, 7B and 7C was weighed and combined according to the directions found below the respective Tables.

Preparation of Solution 3: Using the appropriate balance, each component listed by Table 8 was weighed (using the midpoint of the stated range) and combined according to the directions found below the Table.

Premix-I was then prepared by combining Solution 1 with Solution 2, with mixing, in a ratio of 0.1 ml per liter of final batch volume (end product) to form a combined (1+2) solution. Then, the entire batch of Solution 3 was mixed with the (1+2) solution to produce Premix-I.

Example 6

Preparation of Premix-II

The process of Example 2 was repeated except that the ingredients of Table 9 were used in place of Table 4.

Example 7

Formule-II: Cholesterol-based Nanoparticles by Microfluidation

Formula II was prepared from the Premix-I and Premix-II compositions of Examples 4-6, supra, by following the process of Example 3.

Example 8

Kidney Preservation Evaluation with Formula II

In this study, the solution (composition) of Example 7, designated herein as Formula II, was compared to VIASPAN at 2-8° C. in a static preservation environment using fresh sheep kidneys with +/− hours post harvest cold ischemic damage. Kidneys were removed from a freshly slaughtered sheep and placed immediately on ice. Once returned to the lab, they were aseptically dissected to remove all fatty tissue and isolate the renal artery. Both kidneys were weighed at time =0. The kidneys appeared normal in color, texture and density. Each kidney was flushed until the fluid ran clear, as 100% flush solution, with no trace of blood or other waste material. A biopsy of each respective kidney was taken immediately after it was flushed with solution (T=0). All biopsies were wedges of the outer cortex and greater curvature of the kidney. Each kidney (A & B) was then placed in a container containing the identical solution employed for the flush (either VIASPAN® (kidney A) or Formula-II (kidney B). The individual container was placed in a chiller box opened only for biopsies. Subsequent biopsies were taken at 12, 24, 36, 48, 60, 72 and 96 hours post preservation in either the VIASPAN® or the inventive Formula II solution. Kidney biopsies were preserved in 10% formalin prior to histolopathological evaluation.

Results: there was significant histological differences between the two kidneys. Autolytic (which is the destruction of cells caused by lysine) changes appeared gradually from 12-96 hours post preservation in the VIASPAN treated kidney. There were no histological changes in the kidney treated with the inventive formula II until 36 hours post preservation. It can be seen from the foregoing that the inventive solution offers significant advantages over the prior art when used in hypothermic preservation techniques.

Example 9

Formule-III: Heme-containing Nanoparticles

Stroma-free hemoglobin is obtained from commercial sources or isolated from packed erythrocytes by art-known methods, e.g., as described by U.S. Pat. No. 5,674,528, incorporated by reference herein, and standardized to a concentration of 50% (w/v).

To 200 ml of the stroma-free hemoglobin is added β-NAD (1 mM, 133 mg), D-glucose (100 mM, 3.6 g), ATP-Na (1 mM, 110 mg), magnesium chloride hexahydrate (1 mM, 40 mg), dipotassium hydrogen phosphate (9 mM, 247 mg), disodium hydrogen phosphate (11 mM, 310 mg), and phytic acid (3 mM, 396 mg), and the mixture stirred until the reagents are fully mixed to form a supplemented hemoglobin solution.

To 45 grams of a uniformly mixed powder of purified phosphatydylchorine with a hydrogenation rate of 90%, cholesterol, myristic acid and Vitamin E, in a molar ratio of 7:7:2:0.28, respectively, is added 45 ml of WFI, and the mixture is heated to a temperature of ranging from 60 to about 80° C. to allow for swelling. The above supplemented hemoglobin solution, is added to the resulting lipid material and the mixture agitated for 15 seconds. The resulting lipid-SFH mixed solution is processed through a Microfluidizer 5000 (Microfluidics Co.) and processed in an ice bath at a pressure of 12,000 psi .

The resulting encapsulated hemoglobin is mixed with a saline and dextran solution (3% (w/v)) and the resulting suspension centrifuged at 10,000 rpm (13,000 g)×30 min, at 4° C. The liposomes or nanoparticles with encapsulated hemoglobin are then recovered. The supernatant containing the residual free hemoglobin not encapsulated and/or remaining starting lipid components are removed by decantation or suction. The above-described washing process is repeated until no free hemoglobin remains visible. The resulting product is filtered through a membrane filter with a pore size ranging from 0.2 to 0.45 microns depending on the desired product particle size range. The filtrate is concentrated, e.g., by ultrafiltration through a hollow fiber-type dialyzer for concentration to produce 600 ml of purified hemoglobin-encapsulated liposome or nanoparticle suspension having a hemoglobin concentration of about 5% (w/v).

The resulting liposomes or nanoparticles are mixed with Premix-I in a ratio ranging from about 10 parts to about 500 parts of emulsion, into a total volume of 1000 parts, with Premix-I, to provide Formula-III.

Formula-III is then mixed in a desired ratio with Formula-I, to provide an organ preserving composition with oxygen carrying properties.

Example 10

Cell Culture Media

In this example, the composition of example 3 identified as formula I was tested to prove its ability to function as a cell culture media. Human kidney cells were placed in containers containing a sufficient amount of formula I and cell growth and viability was demonstrated using this material as a cell culture media at 4 and 37 degrees C. After 72 hours, it was demonstrated that viable cells could be grown out to a healthy population of cells showing normal morphology and viability.

The contents of all foregoing U.S. patents and published documents are incorporated herein by reference.

What is claimed:

1. A two-phase composition comprising:
   a first phase comprising a base nutritive medium; and
   a second phase comprising nanoparticles that comprise an outer lipophilic coating and an inner hydrophilic core, wherein
   a) the first phase comprises physiologically compatible concentrations of water soluble or dispersible nutrients, and physiological salts;
   b) the nanoparticles of the second phase comprise lipids, fatty acids, sterols and free fatty acids; and
   c) the two-phase composition has an osmolality of at least about 300 mOsM/kg, and
wherein the nanoparticles have a mean diameter ranging from about 100 nm to about 300 nm, and wherein the hydrophilic inner core of the nanoparticle contains a solution or suspension comprising a moiety capable of binding and releasing oxygen, and the first phase comprises a composition comprising Table 2A or Table 6, wherein
Table 2A is:

|  | g/Liter RANGE |
|---|---|
| Adenosine | 0.950–1.050 |
| Adenosine 5' Monophosphate | 0.0019–0.0021 |
| Adenosine Triphosphate | 0.0019–0.0021 |
| Allopurinol | 0.133–0.147 |
| B' Nicotinamide Adenine Dinucleotide Phosphate | 0.038–0.042 |
| B'Nicotinamide Adenine Dinucleotide | 0.0019–0.0021 |
| Calcium Chloride | 0.152–0.168 |
| Choline Chloride | 0.0085–0.0094 |
| Chondrotin Sulfate | 0.0038–0.0042 |
| Cocarboxylase | 0.038–0.042 |
| Coenzyme A | 0.0095–0.00105 |
| Cyclodextrin | 0.475–0.525 |
| Deoxyadenosine | 0.038–0.042 |
| Deoxycytidine | 0.038–0.042 |
| Deoxyguanosine | 0.038–0.042 |

-continued

|  | g/Liter RANGE |
|---|---|
| Dextran 70 | 33.25–36.75 |
| Flavin Adenine Dinucleotide | 0.038–0.042 |
| Folic Acid | 0.0026–0.0028 |
| Glucose | 3.800–4.200 |
| Glutathione | 0.950–1.050 |
| Glycine | 0.0179–0.0197 |

Table 6 is:

|  | g/Liter |
|---|---|
| Soy Hydrolysate | 6.0–10.0 |
| Glutathione Reduced | 0.008–0.020 |
| Vitamin A Acetate | 0.0002–0.0003 |
| Vitamin C | 0.040–0.060 |
| Vitamin E | 0.00002–0.00003 |
| Catalase | 0.040–0.060 |
| SOD | 0.040–0.060 |
| L-Cysteine HCl | 0.040–0.060 |
| Taurine | 0.025–0.040 |
| Methionine | 0.015–0.030 |
| Zinc Sulfate | 0.0008–0.0009 |
| Selenium | 0.000025–0.000035 |
| Cupric Sulfate | 0.0000045–0.000006 |
| Ethanolamine | 0.0025–0.005 |
| Mercaptoethanol | 0.003–0.006. |

2. The two-phase composition of claim 1 wherein the two-phase composition has an osmolality ranging from about 385-425 mOsM/kg.

3. The two-phase composition of claim 1 wherein the pH of thereof is from about 7.2 to about 7.4.

4. The two-phase composition of claim 1 wherein the nanoparticles have a mean diameter ranging from about 100 nm to about 300 nm.

5. The two-phase composition of claim 4 wherein the nanoparticles have a mean diameter ranging from about 100 nm to about 200 nm.

6. The two-phase composition of claim 1, further comprising cellular growth factors.

7. The two-phase composition of claim 6, wherein said cellular growth factors are selected from the group consisting of epithelial and endothelial growth factors, vascular endothelial growth factors, platelet derived endothelial growth factors, epithelial growth factors, hepatocyte growth factors, and mixtures thereof.

8. The two-phase composition of claim 1 which comprises about equal amounts of the first phase and the second phase.

9. The two-phase composition of claim 1 wherein the outer lipophilic coating comprising a free fatty acid selected grom the group consisting of oleic acid and linoleic acid, and combinations thereof.

10. The two-phase composition of claim 1, which, when comprising Table 2A, further comprises Table 1

|  | g/Liter RANGE |
|---|---|
| Adenine HCl | 0.00019–0.00021 |
| vitamin B-12 | 0.00065–0.0007 |
| Biotin | 0.00000038–0.00000042 |
| Cupric Sulfate | 0.00000124–0.00000137 |

-continued

|  | g/Liter RANGE |
| --- | --- |
| Ferric Nitrate | 0.000048–0.000053 |
| Ferric Sulfate | 0.00048–0.00053 |
| Putrescine HCl | 0.000077–0.000085 |
| Pyridoxine HCl | 0.000029–0.000033 |
| Riboflavin | 0.00021–0.000231 |
| Thymidine | 0.00035–0.00039 |
| Zinc Sulfate | 0.00041–0.000454. |

11. The two-phase composition of claim 1, which when comprising Table 2A further comprises Table 2B, wherein Table 2B is

|  | g/Liter RANGE |
| --- | --- |
| Heparin | 0.171–0.189 |
| HEPES | 3.396–3.753 |
| Hypoxanthine | 0.002–0.0022 |
| Inositol | 0.0124–0.0137 |
| Insulin | 0.0095–0.0105 |
| L-Alanine | 0.00428–0.00473 |
| L-Arginine | 0.141–0.155 |
| L-Asparagine | 0.0076–0.0084 |
| L-Aspartic Acid | 0.064–0.070 |
| L-Cysteine | 0.0297–0.0329 |
| L-Cystine | 0.0167–0.0185 |
| L-Glutamic Acid | 0.007–0.0078 |
| L-Glutamine | 4.750–5.250 |
| L-Histidine | 0.030–0.033 |
| L-Isoleucine | 0.052–0.0572 |
| L-Leucine | 0.057–0.063 |
| L-Lysine | 0.0095–0.0105 |
| L-Methionine | 0.019–0.021 |
| L-Phenylalanine | 0.0337–0.0373 |
| L-Proline | 0.0164–0.0182 |
| L-Serine | 0.025–0.0276 |
| L-Threonine | 0.051–0.056. |

12. The two-phase composition of claim 1, which when comprising Table 2A further comprises Table 2C, wherein Table 2C is

|  | g/Liter RANGE |
| --- | --- |
| L-Tryptophan | 0.009–0.0095 |
| L-Tyrosine | 0.053–0.059 |
| L-Valine | 0.050–0.055 |
| Magnesium Chloride | 0.058–0.0643 |
| Magnesium Sulfate | 0.0475–0.0525 |
| Mannose | 3.135–3.465 |
| Niacinamide | 0.0019–0.0021 |
| Pantothenic Acid | 0.0021–0.0024 |
| Potassium Chloride | 0.296–0.328 |
| Pyridoxal HCl | 0.0019–0.0021 |
| Pyruvic Acid | 0.209–0.231 |
| Sodium Bicarbonate | 1.140–1.260 |
| Sodium Chloride | 6.650–7.350 |
| Sodium Phosphate Dibasic | 0.0676–0.0748 |
| Sodium Phosphate Monobasic | 0.0516–0.0570 |
| Thiamine | 0.0021–0.0023 |
| Transferrin | 0.00475–0.00525 |
| Uridine | 0.038–0.042 |
| Uridine Triphosphate | 0.038–0.042 |
| Yeastolate Ultra-Filtered | 38–42 ML. |

13. The two-phase composition of claim 1, which when comprising Table 2A further comprises Table 3, wherein Table 3 is

|  | g/Liter RANGE |
| --- | --- |
| L-Cystine | 0.0167–0.0185 |
| L-Tyrosine | 0.053–0.059. |

14. The two-phase composition of claim 1, wherein the second phase further comprises Table 4 when the first phase comprises Table 2A, or further comprises Table 9 when the first phase comprises Table 6, and wherein Table 4 is

|  | g/Liter RANGE |
| --- | --- |
| Cholesterol | 0.00475–0.00525 |
| Cod Liver Oil | 0.00095–0.00105 |
| Epithelial Growth Factor | 0.00000285–0.00000315 |
| Hepatocyte Growth Factor | 0.0000048–0.0000053 |
| Hydrocortisone | 0.00095–0.00105 |
| Linoleic Acid | 0.00095–0.00105 |
| Linolenic Acid | 0.00095–0.00105 |
| Oleic Acid | 0.00095–0.00105 |
| Phosphatidylcholine | 0.6% |
| Platelet Derived Endothelial Growth Factor | 0.00000095–0.00000105 |
| Pluronic F-68 | 0.950–1.050 |
| Prostaglandin E1 | 0.000042–0.0000263 |
| Triiodo-L-Thyroxine | 0.00000475–0.0000053 |
| TWEEN 80 ® | 0.002375–0.002625 |
| Vascular Endothelial Growth Factor | 0.0000046–0.00000525 |
| Vitamin E | 0.0019–0.0021 | wherein Table 9 is

| ETOH 95% | 8.00–16.00 ml |
| --- | --- |
| Soy Hydrolysate | 3–8 ml |
| Phosphatidyl Choline | 0.00095–0.010 g/liter |
| Arachadonic Acid | 0.0000015–0.00002 g/liter |
| Linoleic Acid | 0.000095–0.00015 g/liter |
| Linolenic Acid | 0.000095–0.00015 g/liter |
| Myristic Acid | 0.000095–0.00015 g/liter |
| Oleic Acid | 0.000095–0.00015 g/liter |
| Palmitic Acid | 0.000095–0.00015 g/liter |
| Stearic Acid | 0.000095–0.00015 g/liter |
| Cholesterol | 0.002–0.004 g/liter |
| Vitamin E | 0.0006–0.0008 g/liter |
| Tween 80 | 0.020–0.030 g/liter |
| Pluronic F-68 | 0.010–1.000 g/liter. |

15. The two-phase composition of claim 1, which, when comprising Table 6, further comprises Table 7A, wherein Table 7A is

|  | g/Liter RANGE |
| --- | --- |
| Sodium Gluconate | 18.500–25.000 |
| Potassium Phosphate | 3.000–4.500 |
| Magnesium Sulfate | 1.000–1.500 |
| Calcium Chloride | 0.100–0.150 |
| Sodium Phosphate Monobasic | 0.250–0.350. |

16. The two-phase composition of claim 15, which further comprises Table 7B,
wherein Table 7B is

|  | g/Liter RANGE |
|---|---|
| L-Arginine HCl | 0.065–0.080 |
| L-Aspartic Acid | 0.050–0.065 |
| L-Glutamic Acid | 0.100–0.160 |
| L-Glutamine | 0.300–0.400 |
| Glycine | 0.045–0.060 |
| L-Histidine HCl—H$_2$O | 0.155–0.170 |
| L-Isoleucine | 0.025–0.030 |
| L-Leucine | 0.045–0.055 |
| L-Lysine HCl | 0.240–0.300 |
| L-Phenylalanine | 0.045–0.055 |
| L-Proline | 0.045–0.055 |
| L-Threonine | 0.065–0.075 |
| L-Tryptophan | 0.035–0.0450 |
| L-Valine | 0.055–0.070 |
| L-Cystine | 0.018–0.024 |
| L-Tyrosine | 0.050–0.060. |

17. The two-phase composition of claim 15, which further comprises Table 7C
wherein Table 7C is

|  | g/Liter RANGE |
|---|---|
| Glucose | 4.500–6.000 |
| Mannose | 8.000–12.000. |

18. The two-phase composition of claim 15, which further comprises Table 8, wherein
Table 8 is

|  | g/Liter RANGE |
|---|---|
| Biotin | 0.000015–0.00003 |
| Choline Bitartrate | 0.40–0.50 |
| Folic Acid | 0.00035–0.0005 |
| Inositol | 0.0008–0.002 |
| Niacinamide | 0.0008–0.002 |
| Pantothenic Acid | 0.0008–0.002 |
| Pyridoxine | 0.0008–0.002 |
| Riboflavin | 0.0008–0.002 |
| Thiamine | 0.008–0.015 |
| Vitamin B-12 | 0.000015–0.0003 |
| Adenosine | 0.85–1.50. |

19. The two phase composition of claim 1 wherein the moiety capable of binding and releasing oxygen is a heme protein.

20. The two phase composition of claim 1 wherein said hydrophilic inner core contains a biologically active moiety.

21. The two-phase composition of claim 20 wherein said biologically active moiety is selected from the group consisting of chemotherapeutic agents, proteins, peptides, polypeptides, enzymes and mixtures thereof.

22. The three phase composition comprising the composition of claim 1 admixed with a composition comprising a nonoparticle having an outer lipophilic coating and a hydrophilic inner core comprising a solution or suspension comprising a moiety capable of binding and releasing oxygen.

23. The three phase composition of claim 22 wherein the moiety capable of binding and releasing oxygen is a heme protein.

24. A three phase composition comprising the composition of claim 1 admixed with a composition comprising a nanoparticle having an outer lipophilic coating and a hydrophilic inner core comprising a biologically active moiety.

25. A process for preparing the two phase composition of claim 1 comprising combining a liquid first phase comprising a base nutritive medium containing physiologically compatible concentrations of water soluble or dispersible nutrients, and physiological salts with a liquid second phase comprising nanoparticles that comprise an outer lipophilic coating and an inner hydrophilic core under conditions sufficient to prepare a final two phase composition having an osmolality of at least about 300 mOsM/kg.

26. A method of preserving a mammalian cells or tissues, comprising placing said cells or said tissue in a sufficient amount of the composition of claim 1.

27. A method of preserving a mammalian kidney, ex vivo, comprising perfusing the kidney with an effective amount of the composition of claim 1.

28. A method of maintaining the health of a member of the group consisting of mammalian cells and tissues ex vivo, comprising placing said member in a sufficient amount of a composition of claim 1 and maintaining said member at a non-hypothermic temperature.

29. The method of claim 28 wherein non-hypothermic temperature ranges from about 20 to 37° C.

* * * * *